(12) United States Patent
Tashiro et al.

(10) Patent No.: US 8,002,449 B2
(45) Date of Patent: Aug. 23, 2011

(54) LIGHT SOURCE APPARATUS FOR ENDOSCOPE

(75) Inventors: Yosuke Tashiro, Tokyo (JP); Yuya Masukawa, Saitama (JP)

(73) Assignee: Hoya Corporation, Tokyo (JP)

( * ) Notice: Subject to any disclaimer, the term of this patent is extended or adjusted under 35 U.S.C. 154(b) by 358 days.

(21) Appl. No.: 12/419,443

(22) Filed: Apr. 7, 2009

(65) Prior Publication Data

US 2009/0290374 A1 Nov. 26, 2009

(30) Foreign Application Priority Data

Apr. 8, 2008 (JP) ................................. 2008-100241

(51) Int. Cl.
*A61B 1/06* (2006.01)
*F21V 5/00* (2006.01)

(52) U.S. Cl. ........ 362/574; 362/276; 362/285; 362/418; 600/101; 600/178

(58) Field of Classification Search .................. 362/574, 362/276, 411, 394, 295, 572, 802, 804, 249.03, 362/249.07, 285, 286, 418, 422; 600/101, 600/160, 178, 189, 180
See application file for complete search history.

(56) References Cited

U.S. PATENT DOCUMENTS

| 4,433,675 A * | 2/1984 | Konoshima ................... 600/178 |
| 4,729,018 A * | 3/1988 | Watanabe et al. ............... 348/69 |
| 5,833,343 A | 11/1998 | Nakano et al. |
| 7,160,014 B2 * | 1/2007 | Sasaki et al. .................. 362/574 |
| 7,828,726 B2 * | 11/2010 | Negishi ......................... 600/178 |
| 2003/0001952 A1 | 1/2003 | Iida et al. |
| 2003/0156430 A1 * | 8/2003 | Ota et al. ...................... 362/574 |
| 2006/0052214 A1 | 3/2006 | Ito |
| 2006/0088303 A1 | 4/2006 | Ito |
| 2006/0287581 A1 | 12/2006 | Ito |
| 2007/0010712 A1 * | 1/2007 | Negishi ......................... 600/178 |
| 2007/0010714 A1 * | 1/2007 | Negishi ......................... 600/180 |
| 2007/0093688 A1 | 4/2007 | Enomoto |
| 2007/0253215 A1 | 11/2007 | Takahashi et al. |

FOREIGN PATENT DOCUMENTS

| JP | 3-48565 | 10/1991 |
| JP | 9-10174 | 1/1997 |

OTHER PUBLICATIONS

English language Abstract of JP 9-10174, Jan. 14, 1997.

* cited by examiner

*Primary Examiner* — Bao Q Truong
(74) *Attorney, Agent, or Firm* — Greenblum & Bernstein P.L.C.

(57) ABSTRACT

A light source apparatus, configured to introduce light into an endoscope connected thereto, includes a housing, a plurality of light sources supported movably relative to the housing, the light sources being configured to emit light, a light introducing unit configured to introduce, into the endoscope, the light emitted by an intended one of the light sources which is located in such a position that an optical axis thereof corresponds to an optical axis of the light introducing unit, a detector configured to detect a misalignment between the optical axis of the light introducing unit and the optical axis of the intended light source, and a light source moving unit configured to move the intended light source to such a position that the optical axis of the intended light source corresponds to the optical axis of the light introducing unit when the misalignment is detected by the detector.

11 Claims, 6 Drawing Sheets

LIGHT SOURCE APPARATUS FOR ENDOSCOPE

BACKGROUND OF THE INVENTION

The following description relates to one or more light source apparatuses for an endoscope which apparatuses are adapted to appropriately change light sources for supplying light to the endoscope.

As a system employed when a doctor observes the inside of a body cavity of a patient, generally known is a system to observe, on a monitor, an image of the inside of the body cavity captured through an electronic scope, or a system to directly observe the inside of the body cavity through a fiber scope. Such an observation system has a light source apparatus configured to introduce light into a Light Carrying Bundle (LCB) of the electronic scope or the fiber scope and to illuminate, through the LCB, the inside of the body cavity where natural light cannot be introduced. The light source apparatus is loaded with a high-intensity lamp, as a light source, such as a xenon lamp, a halogen lamp, a mercury lamp, and a metal halide lamp.

In the meantime, the light source of the light source apparatus may be turned off due to the end of life or malfunction of the light source while an inspection or an operation is being implemented for the inside of the body cavity with the electronic scope or the fiber scope inserted into the body cavity. In this situation, the doctor cannot visually recognize the inside of the body cavity. Thus, it results in not only a problem that the inspection or the operation cannot be continued but as well a problem that it becomes harder to pull the electronic scope or the fiber scope out of the body cavity.

As a solution for the aforementioned problems, there has been proposed a light source apparatus which includes a plurality of light sources. In the case where such a light source apparatus is used, even though a currently-used one of the light sources is turned off due to the end of life or the malfunction during the inspection or the operation, it is possible to continuously illuminate the inside of the body cavity by quickly changing the currently-used light source to another one. For instance, Japanese Patent Provisional Publication No. HEI9-10174 (hereinafter, simply referred to as '174 Publication) exemplifies a light source apparatus provided with a plurality of light sources.

The light source apparatus of '174 Publication is loaded with two light sources, and provided with a turning table rotatably supported. The turning table has an outer circumferential gear formed on an outer circumference thereof, which gear is configured to engage with a gear attached to a shaft of a stepping motor. The stepping motor is configured to rotate the turning table through the aforementioned gears that engage with each other. Further, the stepping motor is controlled to stop one of the light sources in such a position on an optical axis of the LCB as to get light introduced into the LCB at the highest efficiency. Then, the light source (more exactly, the turning table) is held in the stop position by a holding force of the stepping motor.

SUMMARY OF THE INVENTION

In the stepping motor, the holding force is reduced with no electricity supplied to the stepping motor. For example, when the light source apparatus is transported or conveyed, or vibrated due to an earthquake, the stepping motor might fail to hold the turning table, and thus the turning table might be rotated. However, the above '174 Publication does not raise such a problem regarding unintentional rotation of the turning table (in other words, a problem of misalignment between the optical axes of the light source and the LCB). In addition, a manual type (see Japanese Utility Model Provisional Publication No. HEI3-48565) has mainly been employed as a mechanism for changing the light source. So far, therefore, there has been no study to present a solution for the problem (i.e., the misalignment between the optical axes of the light source and the LCB in the light source apparatus having the electrically driven mechanism for changing the light source).

Aspects of the present invention are advantageous to provide one or more light source apparatuses for an endoscope that make it possible to effectively avoid a misalignment between optical axes from an intended one of light sources to an endoscope, even though an electrically driven mechanism for changing the light sources is applied.

According to aspects of the present invention, a light source apparatus is provided which is configured to introduce light into an endoscope connected thereto. The light source apparatus includes a housing, a plurality of light sources supported movably relative to the housing, the light sources being configured to emit light, a light introducing unit configured to introduce, into the endoscope, the light emitted by an intended one of the light sources which is located in such a position that an optical axis thereof corresponds to an optical axis of the light introducing unit, a detector configured to detect a misalignment between the optical axis of the light introducing unit and the optical axis of the intended light source, and a light source moving unit configured to move the intended light source to such a position that the optical axis of the intended light source corresponds to the optical axis of the light introducing unit when the misalignment is detected by the detector.

Optionally, the light source apparatus may include a light source holder configured to hold the light sources, which light source holder is supported movably relative to the housing. In this case, the light source moving unit may be configured to move the light source holder to change positions of the light sources relative to the light introducing unit.

Further optionally, the light source holder may include a rotating disk supported rotatably relative to the housing. In this case, the light sources may be attached to the rotating disk. Further, the light source moving unit may be configured to rotate the rotating disk to change the positions of the light sources relative to the light introducing unit. Furthermore, the detector may include a hole formed in such a position on the rotating disk as to correspond to a position of each of the light sources in a radial direction of the rotating disk, a photo sensor configured to detect the hole, and a sensor output detector configured to detect the misalignment based on a detection result of the photo sensor.

Optionally, the light source apparatus may include a switch configured to select therethrough one of the light sources as the intended light source. In this case, the detector may be configured to detect the misalignment between the optical axis of the light introducing unit and the optical axis of the intended light source selected through the switch.

Yet optionally, the light source apparatus may further include an electrical power supply configured to supply an electrical power required for emitting light, selectively to the intended light source selected through the switch.

Optionally, the light introducing unit may include a converging optical system configured to converge the light emitted by the intended light source and to introduce the converged light into a Light Carrying Bundle (LCB) of the endoscope.

Still optionally, the light source moving unit may include a motor configured to generate a rotational driving force for rotating the rotating disk, and a roller configured to transmit the rotational driving force from the motor to the rotating disk such that the rotating disk is rotated.

Further optionally, the motor may be a DC motor.

Optionally, the light source apparatus may further include a locking mechanism configured to lock the light source holder in such a position that the optical axis of the intended light source held by the light source holder corresponds to the optical axis of the light introducing unit when the light source moving unit does not move the light source holder.

Optionally, the light source apparatus may further include a locking mechanism configured to lock the rotating disk in such a position that the optical axis of the intended light source attached to the rotating disk corresponds to the optical axis of the light introducing unit when the light source moving unit does not rotate the rotating disk.

Still optionally, the locking mechanism may include a first magnetic member fixed relative to the housing, and a second magnetic member provided to the rotating disk, the second magnetic member being configured to establish contact with the first magnetic member through rotation of the rotating member. In this case, the intended light source may be firmly positioned relative to the light introducing unit by the second magnetic member stuck to the first magnetic member due to a magnetic attractive force generated therebetween when the light source moving unit does not rotate the rotating disk.

DETAILED DESCRIPTION OF THE EMBODIMENTS

It is noted that various connections are set forth between elements in the following description. It is noted that these connections in general and, unless specified otherwise, may be direct or indirect and that this specification is not intended to be limiting in this respect.

Hereinafter, an electronic endoscope system of an embodiment according to aspects of the present invention will be described with reference to the accompanying drawings.

Figure 1:
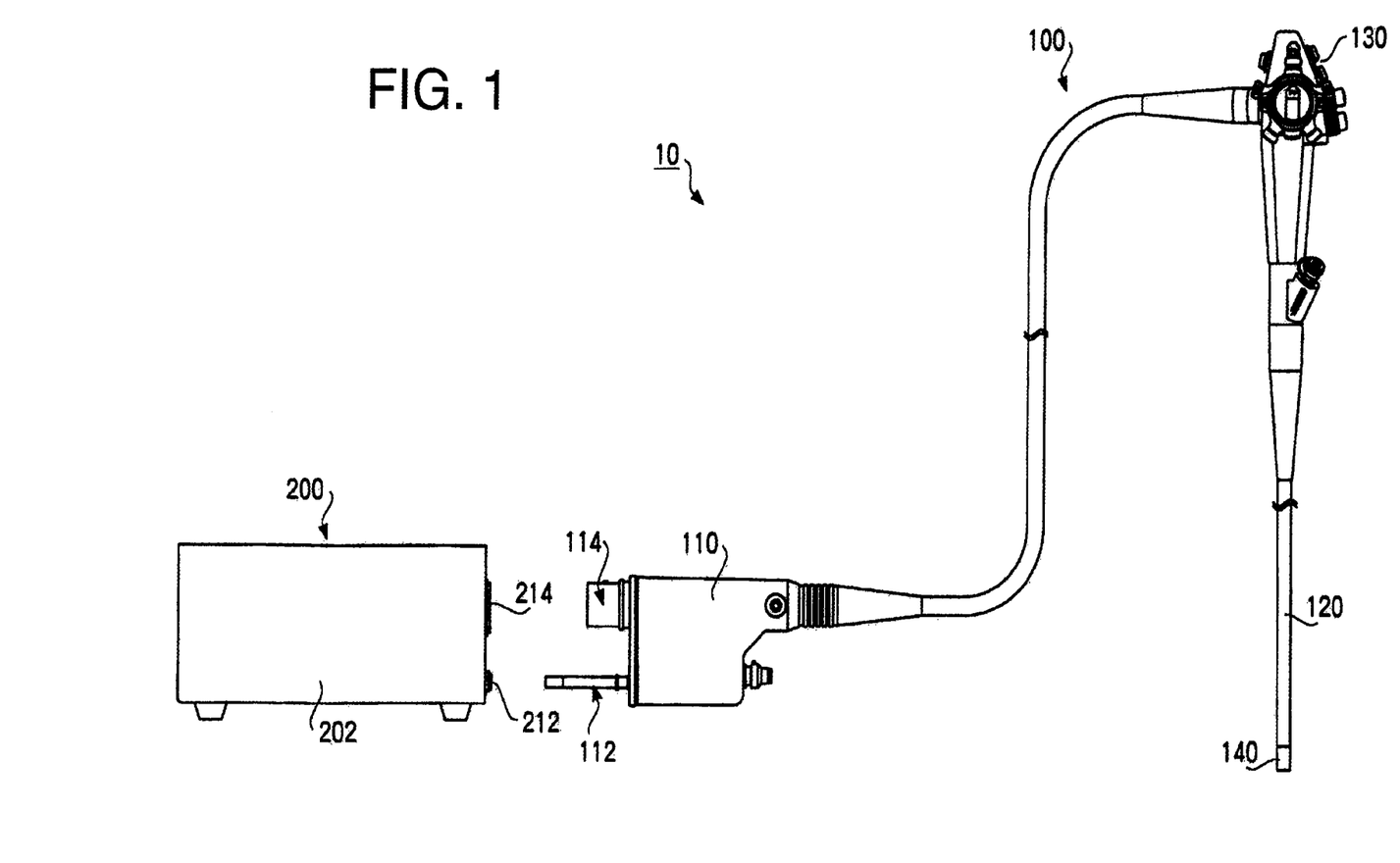
FIG. 1 is an external view of an electronic endoscope system in an embodiment according to one or more aspects of the present invention.
Figure 2:
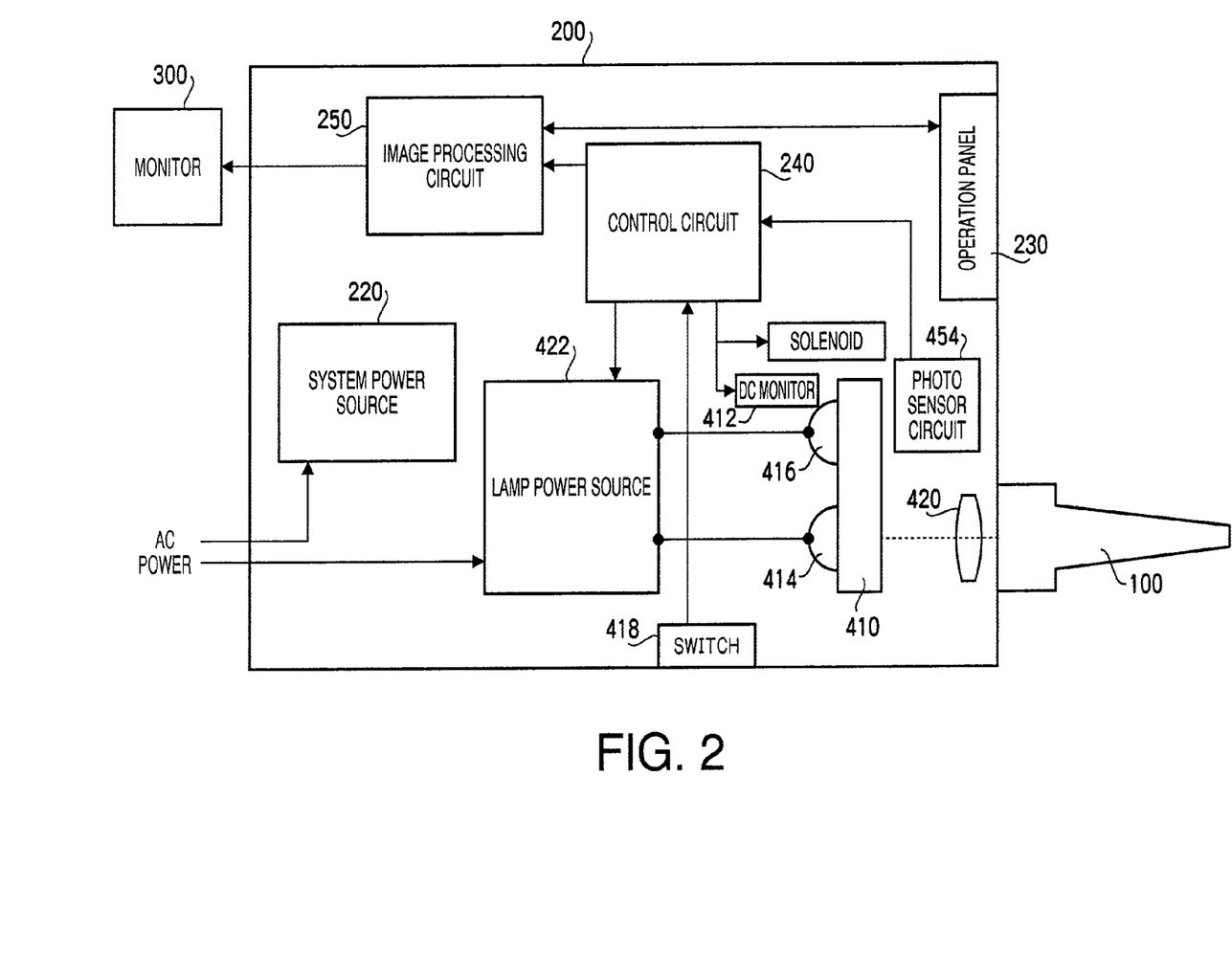
FIG. 2 is a block diagram of the electronic endoscope system in the embodiment according to one or more aspects of the present invention.

FIG. 1 is an external view of an electronic endoscope system 10 in an embodiment according to aspects of the present invention. FIG. 2 is a block diagram of the electronic endoscope system 10. As illustrated in FIGS. 1 and 2, the electronic endoscope system 10 includes an electronic scope 100, a processor 200, and a monitor 300. It is noted that the monitor 300 is not shown in FIG. 1 for the sake of simplicity.

Figure 3:
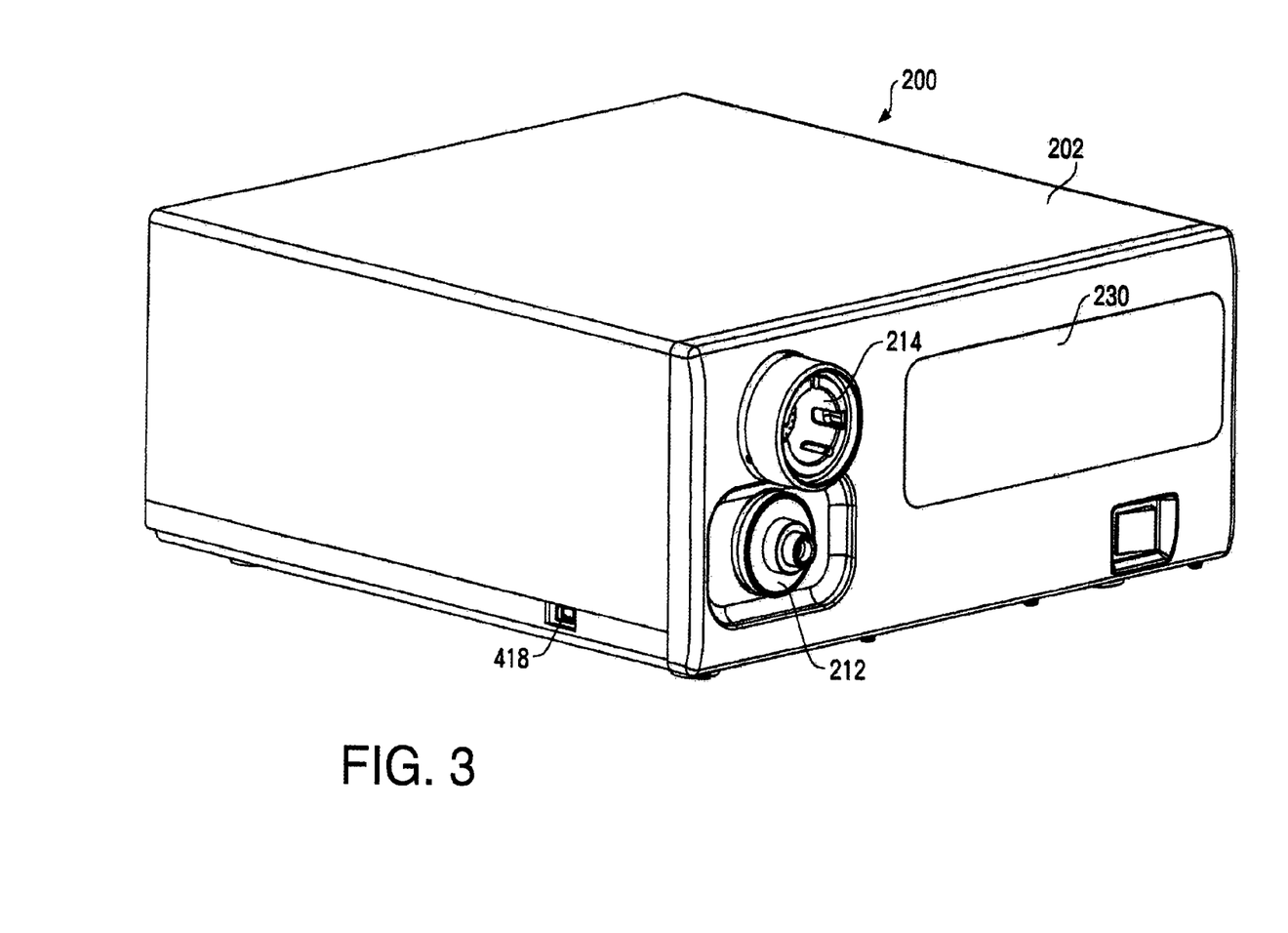
FIG. 3 is an external perspective view showing a processor of the electronic endoscope system in the embodiment according to one or more aspects of the present invention.

FIG. 3 is a perspective view showing an external appearance of the processor 200. The processor 200 is integrated with a signal processor and a light source apparatus incorporated therein. The signal processor is configured to process a signal issued by the electronic scope 100. Further, the light source apparatus is configured to get light introduced into a Light Carrying Bundle (LCB: not shown) of the electronic scope 100 and to illuminate through the LCB the inside of a body cavity where natural light cannot be introduced. It is noted that, in another embodiment, the signal processor and the light source apparatus are configured as respective separate bodies. FIG. 2 shows elements contained in the processor 200 provided with the light source apparatus, yet does not show any elements contained in the electronic scope 100 or the monitor 300 for the sake of simplicity.

As illustrated in FIG. 1, a connector unit 110 is provided at an anchor portion of the electronic scope 100. The connector unit 110 is provided with an LCB connecting plug 112 and a signal connecting plug 114. When the LCB connecting plug 112 is plugged into an LCD connecting jack 212 of the processor 200, the electronic scope 100 is optically linked with the processor 200. In addition, when the signal connecting plug 114 is plugged into a signal connecting jack 214 of the processor 200, the electronic scope 100 is electrically joined with the processor 200. The processor 200 and the monitor 300 are electrically connected via a predetermined cable.

As illustrated in FIG. 2, the processor 200 has a system power source 220, which is configured to appropriately transform up or down a voltage from a commercial power supply and to supply an electrical power to the electronic scope 100 and the monitor 300 as well as circuits of the processor 200. It is noted that, in FIG. 2, wire connections (such as connections between the system power source 220 and circuits of the processor 200) are partially omitted for the sake of illustrative simplicity and convenience.

When the connections between the processor 200 and both the electronic scope 100 and the monitor 300 are established, an operator can implement an inspection and/or an operation for the inside of a body cavity of a patient with the electronic endoscope system 10. Specifically, the operator inserts a bendable insertion part 120 of the electronic scope 100 into the body cavity. Then, while operating an operation part 130 of the electronic scope 100, the operator introduces a distal end portion 140 of the electronic scope 100 to a region around an observed object. When the distal end portion 140 reaches the observed object, the operator operates the operation part 130 and an operation panel 230 provided at a front face of the processor 200. The operator performs the inspection and the operation while observing on the monitor 300 an image of the inside of the body cavity obtained through the above operations.

The processor 200 has a rotating disk 410 supported rotatably relative to a housing 202 of the processor 200. The rotating disk 410 is loaded with two light sources 414 and 416 adapted to emit white light, and configured to be rotated by a DC motor 412. A high-intensity lamp such as a xenon lamp, a halogen lamp, a mercury lamp, and a metal halide lamp is suitable for the light sources 414 and 416.

The rotation of the rotating disk 410 is controlled by a control circuit 240, which is configured to take overall control of the entire processor 200. The processor 200 includes a switch 418 provided at a side face thereof. When the switch 418 is operated by the operator, a signal depending on the switching operation of the switch 418 is inputted into the control circuit 240. The control circuit 240 drives the CD motor 412 in accordance with the inputted signal to rotate the rotating disk 410. The rotating disk 410 is rotated in response to the switching operation of the switch 418. Then the rotating disk 410 is stopped and held in a position where the optical axis (a below-presented optical axis 414AX or 416AX in FIG. 5) of one of the light sources 414 and 416 selected according to the switching operation corresponds to the optical axis of a converging lens 420. The rotating disk 410 and a structure therearound will be described in detail below.

The light sources 414 and 416 are supplied with voltage from the commercial power supply via the lamp power source 422. The control circuit 240 controls the lamp power source 422, while monitoring an input signal from the switch 418, such that the voltage is supplied only to one of the light sources 414 and 416 that faces the converging lens 420 (more specifically, one of the light sources 414 and 416 that is located to have a common optical axis with the converging lens 420. Therefore, white light, which is emitted by the one of the light sources 414 and 416 that is supplied with the voltage, is rendered incident to the converging lens 420 and converged through the converging lens 420. The light converged through the converging lens 420 is introduced into the LCB held inside the LCB connecting plug 112 from an inlet end of the LCB. It is noted that the signal connecting jack 214 and the LCB connecting jack 212 located in front of the converging lens 420 are omitted in FIG. 2 for the sake of simplicity.

The light introduced into the LCB is transmitted through the LCB to the distal end of the electronic scope 100, and emitted from an outlet end of the LCB. Then, the light is emitted by a light distribution lens provided at a front face of the distal end portion 140 to illuminate the observed object. The light is partially reflected by the observed object, and then incident to an objective lens provided at the front face of the distal end portion 140. The light incident to the objective lens is converged to form an optical image on a light receiving surface (pixels) of an imaging device.

The imaging device is, for example, a single plate color CCD with a Bayer pixel array, which is configured to accumulate an electric charge proportional to the light intensity of the optical image formed on each pixel and convert the charge into a voltage (a color signal). The converted color signal is inputted into an image processing circuit 250 via the signal connecting plug 114 and the signal connecting jack 214. It is noted that an insulating circuit using a photo-coupler is disposed next to the signal connecting jack 214 such that the electronic scope 100 is electrically isolated from the processor 200.

The color signal inputted into the image processing circuit 250 is converted, through predetermined image processing by the image processing circuit 250, into a video signal such as a composite video signal and an S video signal, and then transmitted to the monitor 300. Thereby, an image of the inside of the body cavity of the patient is displayed on the monitor 300, and it enables the operator to observe the inside of the body cavity.

Subsequently, the structure around the rotating disk 410, namely, the light source apparatus will be described in detail.

Figure 4:
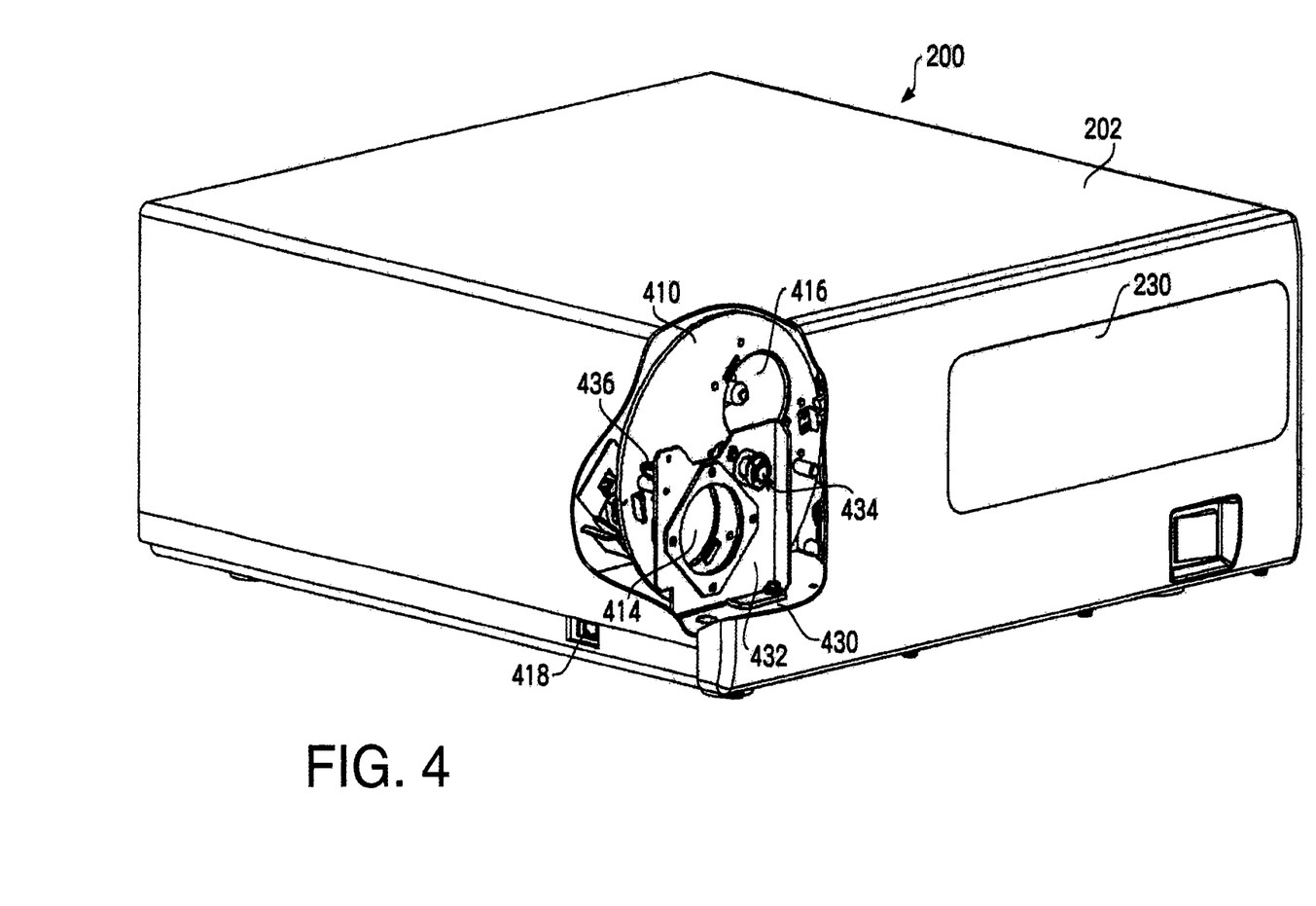
FIG. 4 is a perspective view partially showing a structure inside the processor in the embodiment according to one or more aspects of the present invention.

FIG. 4 is a perspective view of the processor 200, which is provided with an opening formed at a part of the housing 202 for illustrative purposes so as to visually recognize the structure around the rotating disk 410. As illustrated in FIG. 4, a base 430 is fixed to the housing 202 with screws. Further, a supporting plate 432 is fixed to the base 430 with screws. The supporting plate 432 is disposed between the rotating disk 410 and the converging lens 420. The supporting plate 432 is formed with an opening 432ap (see FIG. 5) through which white light emitted by the light source 414 or 416 passes.

The supporting plate 432 has a bearing to support a shaft 434. The rotating disk 410 is, rotatably around the shaft 434, supported by the supporting plate 432 via the shaft 432. It is noted that the base 430 and the supporting plate 432 are components fixedly positioned relative to the housing 202, and may be designed as components formed integrally with the housing 202. In the embodiment, such components supported by or fixed to components fixedly positioned relative to the housing 202 are regarded as components supported by or fixed to the housing 202. For instance, a below-mentioned permanent magnet 436 provided to the supporting plate 432 is regarded as a component provided to the housing 202.

Figure 5:
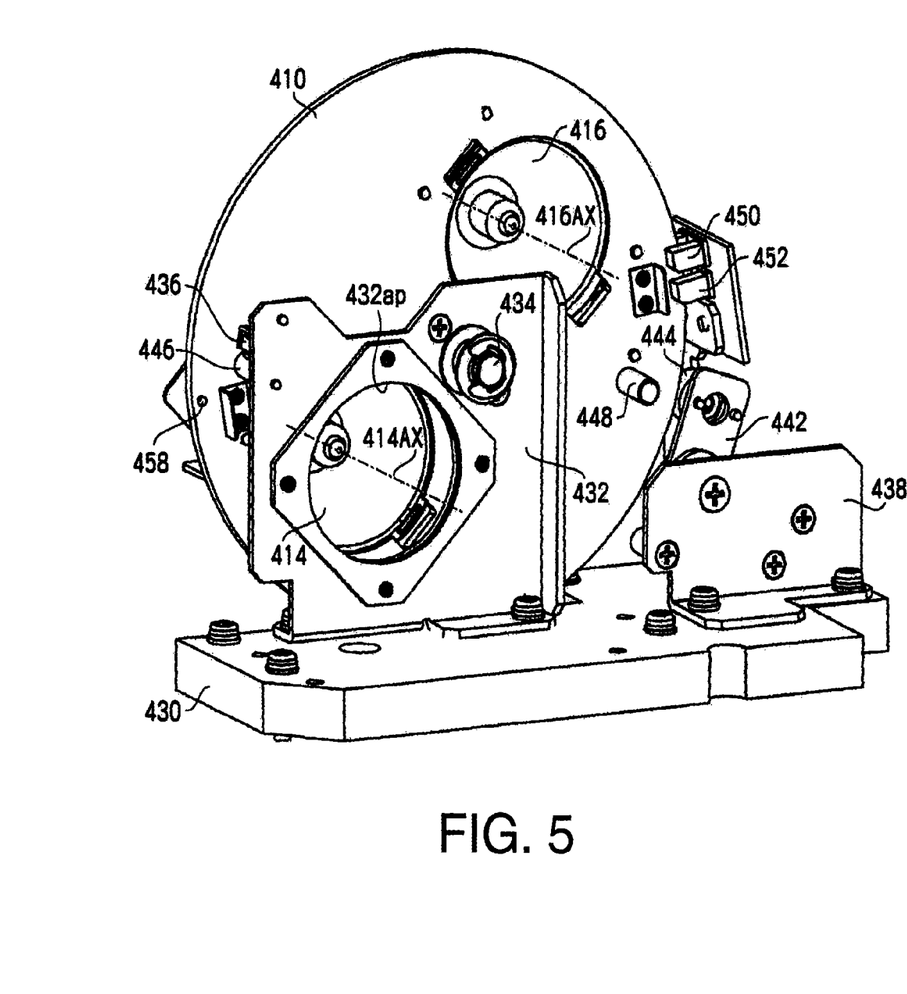
FIG. 5 is a perspective view showing a structure around a rotating disk inside the processor in the embodiment according to one or more aspects of the present invention.

FIG. 5 is a perspective view to show the structure around the rotating disk 410 as a partial structure inside the processor 200. As illustrated in FIG. 5, a supporting plate 438 is fixed to the base 430 with screws. In addition, a solenoid 440 is attached to the supporting plate 438 (see FIG. 6). It is noted that the solenoid 440 is placed in such a position as to be hidden behind the supporting plate 438 in FIG. 5.

A plunger 440p of the solenoid 440 (see FIGS. 6 and 7) is attached with an arm 442. Additionally, a distal end of the arm 442 is attached with a pinch roller 444. The pinch roller 444 is supported by a shaft (not shown) of the DC motor 412. The pinch roller 444 is pressed against a side circumferential surface of the rotating disk 410 under a predetermined pressure. The pinch roller 444 is rotated by the DC motor 412 that is driven by the control circuit 240. Further, the pinch roller 444 transmits a rotational driving force from the DC motor 412 to the rotating disk 410, and thereby the rotating disk 410 is rotated. The pinch roller 444 is desired to be formed with rubber material that has such a high frictional coefficient as to prevent the pinch roller 444 from slipping relative to the rotating disk 410 being revolving. More specifically, the pinch roller 444 is preferred to be formed with rubber material that has such a frictional coefficient as to meet the aforementioned requirement and further to keep a torque of the DC motor 412 as low as possible.

Figure 6:
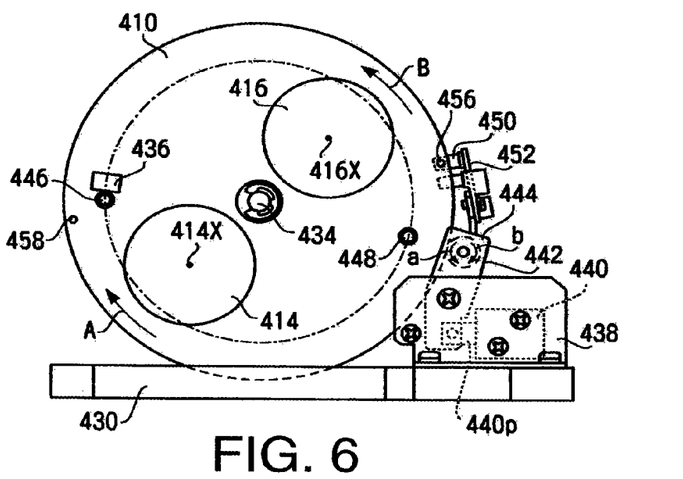
FIG. 6 is an elevational view showing the structure around the rotating disk in the embodiment according to one or more aspects of the present invention.

FIG. 6 is an elevational view of the structure around the rotating disk 410 when viewed from a front side of the processor 200). It is noted that FIG. 6 is intended to illustrate a rotational operation of the rotating disk 410, and thus shown in a more simplified manner than FIG. 5 for the sake of illustrative convenience. Furthermore, in FIG. 6, the supporting plate 432 is omitted while the permanent magnet 436 is shown which is provided on a surface of the supporting plate 432 that faces the rotating disk 410. As illustrated in FIG. 6, the rotating disk 410 is rotated in a direction indicated by an arrow "A" when the pinch roller 444 revolves in a direction indicated by an arrow "a." Meanwhile, the rotating disk 410 is rotated in a direction indicated by an arrow "B" when the pinch roller 444 revolves in a direction indicated by an arrow "b."

Here, magnetic pins 446 and 448 are provided on a surface of the rotating disk 410 that faces the supporting plate 432. The magnetic pins 446 and 448 are configured to protrude toward the supporting plate 432 in a direction along an optical axis (e.g., the optical axis 414AX) and to have a length, in a direction perpendicular to the rotating disk 410, enough to contact the permanent magnet 436. Moreover, the magnetic pins 446 and 448 and the permanent magnet 436 are disposed substantially on a common circle defined on the rotating disk 410 around the shaft 434, as indicated by an alternate long and short dash line in FIG. 6. Accordingly, when the rotating disk 410 is rotated, one of the magnetic pins 446 and 448 comes into contact with the permanent magnet 436 and then sticks to the permanent magnet 436. Thereby, the rotating disk 410 is stopped and certainly held in the stop position by an attractive force between the magnetic pin 446 or 448 and the permanent magnet 436.

More specifically, when the light source 414 is selected through the switch 418, the pinch roller 444 rotates in the direction of the arrow "a," and thereby the rotating disk 410 is rotated in the direction of the arrow "A." Then, the magnetic pin 446 comes into contact with the permanent magnet 436 and sticks to the permanent magnet 436. Here, the magnetic pin 446 is disposed such that the optical axis 414AX corresponds to the optical axis of the converging lens 420 when sticking to the permanent magnet 436. Further, as described above, when the light source 414 is selected through the switch 418, the control circuit 240 controls the light source 414 to emit white light. Therefore, the white light emitted by the light source 414 is rendered incident to the converging lens 420 through the opening 432ap, converged by the converging lens 420, and introduced into the LCB of the electronic scope 100.

Further, when the light source 416 is selected through the switch 418, the pinch roller 444 rotates in the direction of the arrow "b," and thereby the rotating disk 410 is rotated in the direction of the arrow "B." Then, the magnetic pin 448 comes into contact with the permanent magnet 436 and sticks to the permanent magnet 436. Here, the magnetic pin 448 is disposed such that the optical axis 416AX corresponds to the optical axis of the converging lens 420 when sticking to the permanent magnet 436. Further, as described above, when the light source 416 is selected through the switch 418, the control circuit 240 controls the light source 416 to emit white light. Therefore, the white light emitted by the light source 416 is rendered incident to the converging lens 420 through the opening 432ap, converged by the converging lens 420, and introduced into the LCB of the electronic scope 100.

The magnetic pins 446 and 448 are disposed of the common circle, which is indicated by the alternate long and short dash line in FIG. 6, on the surface of the rotating disk 410 at intervals of 180 degrees. Therefore, the rotational angle of the rotating disk 410 is regulated up to 180 degrees in each of the direction of the arrow "A" and the direction of the arrow "B," by the mechanical interference between the magnetic pin 446 or 448 and the permanent magnet 436.

In the meantime, when the DC motor 412 is driven until the magnetic pin 446 or 448 comes into contact with the permanent magnet 436, it causes a great impact at the time of the collision between the magnetic pin 446 or 448 and the permanent magnet 436. In order to reduce the impact, the structure around the rotating disk 410 is configured as follows.

The structure around the rotating disk 410 is provided with photo sensors 450 and 452 such as photo interrupters, each of which includes a light emitting element and a light receiving element disposed to face one another via the rotating disk 410. The photo sensors 450 and 452 are configured to be connected with a photo sensor circuit 454 and to transmit an output signal to the control circuit 240 via the photo sensor circuit 454. Sensor detection holes 456 and 458 that correspond to the photo sensors 450 and 452, respectively, are formed at an outer circumferential portion of the rotating disk 410.

The sensor detection hole 456 is formed in such a position as to be detected by the photo sensor 450 when the optical axis 414AX is located substantially on the optical axis of the converging lens 420. Therefore, when the rotating disk 410 is rotated in the direction of the arrow "A," and the magnetic pin 446 gets close to the permanent magnet 436 (in other words, just before the magnetic pin 446 collides against the permanent magnet 436), only the photo sensor 450 of the two photo sensors is put in a transmitted state where light emitted by the light emitting element of the photo sensor 450 is transmitted through the sensor detection hole 456 to the light receiving element of the photo sensor 450. When a sensor output at this time is inputted into the control circuit 240, the control circuit 240, as described later, controls the pinch roller 444 to get away from the side circumferential surface of the rotating disk 410 and controls the DC motor 412 to stop. Thereby, since the rotating disk 410 does not receive any rotational driving force from the pinch roller 444 or the DC motor 412, the rotational speed of the rotating disk 410 is decelerated. Consequently, the magnetic pin 446 sticks to the permanent magnet 436 with little impact (substantially no impact). The rotating disk 410 cannot further be rotated in the direction of the arrow "A" due to the mechanical interference between the magnetic pin 446 and the permanent magnet 436. Therefore, the sensor detection hole 456 cannot reach the detecting position of the photo sensor 452. The photo sensors 450 and 452 are respectively in the transmitted state and in a shielded state where the light emitted by the light emitting element of the photo sensor 452 is blocked by the rotating disk 410, when the magnetic pin 446 is stuck to the permanent magnet 436.

Furthermore, the sensor detection hole 458 is formed in such a position as to be detected by the photo sensor 452 when the optical axis 416AX is located substantially on the optical axis of the converging lens 420. Therefore, when the rotating disk 410 is rotated in the direction of the arrow "B," and the magnetic pin 448 gets close to the permanent magnet 436 (in other words, just before the magnetic pin 448 collides against the permanent magnet 436), only the photo sensor 452 among the two photo sensors is put in a transmitted state where light emitted by the light emitting element of the photo sensor 452 is transmitted through the sensor detection hole 458 to the light receiving element of the photo sensor 452. When a sensor output at this time is inputted into the control circuit 240, the control circuit 240, as described later, controls the pinch roller 444 to get away from the side circumferential surface of the rotating disk 410 and controls the DC motor 412 to stop. Thereby, since the rotating disk 410 does not receive any rotational driving force from the pinch roller 444 or the DC motor 412, the rotational speed of the rotating disk 410 is decelerated. Consequently, the magnetic pin 448 sticks to the permanent magnet 436 with little impact (substantially no impact). The rotating disk 410 cannot further be rotated in the direction of the arrow "B" due to the mechanical interference between the magnetic pin 448 and the permanent magnet 436. Therefore, the sensor detection hole 458 cannot reach the detecting position of the photo sensor 450. The photo sensors 450 and 452 are respectively in a shielded state where the light emitted by the light emitting element of the photo sensor 450 is blocked by the rotating disk 410 and the transmitted state, when the magnetic pin 448 is stuck to the permanent magnet 436.

It is noted that the structure around the rotating disk 410 is designed such that the center of the sensor detection hole 456 or 458 is located on the optical path between the light emitting element and the light receiving element of the photo sensor 450 when the optical axis 414X or 416AX completely corresponds to the optical axis of the converging lens 420, with no consideration of a tolerance of each component included in the structure. However, in a modification according to aspects of the present invention, the structure around the rotating disk 410 may be designed such that the sensor detection holes 456 and 458 are slightly shifted upstream in the rotational directions of the arrow A and the arrow B, respectively. Such a design can result in earlier detection of the magnetic pin 446 or 448 getting closer to the permanent magnet 436 during the rotation of the rotating disk 410. Hence, the impact caused by the collision between the permanent magnet 436 and the magnetic pin 446 or 448 can be reduced.

As described above, the control circuit 240 controls the lamp power source 422 in conjunction with the switch 418 to supply an electrical power to one of the light sources 414 and 416. However, as a modification according to aspects of the present invention, the control circuit 240 may be configured to control the lamp power source 422 while monitoring the sensor outputs of the photo sensors 450 and 452. Specifically, the control circuit 240 may control the lamp power source 422 to supply an electrical power only to the light source 414 when the photo sensors 450 and 452 are in the transmitted state and the shielded state, respectively.

For example, when the processor 200 is transported or transferred, or when an earthquake occurs, the rotational disk 410 might receive a vibration beyond the attractive force between the permanent magnet 436 and the magnetic pin 446 or 448. At this time, the state of the magnetic pin 446 or 448 sticking to the permanent magnet 436 cannot be maintained, and thereby the rotational disk 410 is rotated to cause the misalignment between the optical axis 446 or 448 and the optical axis of the converging lens 420. It leads to a reduced intensity (or substantially no intensity) of the light introduced into the LCB of the electronic scope 100. Thus, the inside of the body cavity cannot sufficiently be illuminated, and it results in a problem in the inspection or the operation for the inside of the body cavity.

In order to solve the problem, the control circuit 240 monitors the sensor outputs of the photo sensors 450 and 452. When the photo sensor 450 (or 452) is in the shielded state (for instance, at the time when the processor 200 is powered on), or comes into the shielded state (for instance, during the inspection or the operation), with the light source 414 (or 416) selected through the switch 418, the control circuit 240 detects that the optical axis 414AX (or 416AX) is misaligned relative to the optical axis of the converging lens 420. When detecting the misalignment of the optical axes, the control circuit 240 drives the DC motor 412 to rotate the rotating disk 410 in the direction of the arrow "A" (or in the direction of the arrow "B") and to place the light source 414 (or 416) back into the position where the optical axis 414AX (or 416AX) corresponds to the optical axis of the converging lens 420. By such closed loop control, an unintended misalignment between the optical axes caused due to an external factor can quickly be corrected, and thus it is possible to effectively prevent the intensity of the light introduced into the LCB of the electronic scope 100 from decreasing.

It is noted that, when the DC motor 412 is driven to be stopped, the rotation of the rotating disk 410 might be stopped immediately before the magnetic pin 446 or 448 comes into contact with the permanent magnet 436. In this case, since the rotating disk 410 is not held by the attractive force between the permanent magnet 436 and the magnetic pin 446 or 448, there is a problem that the rotating disk 410 is easily rotated by an external force. In order to avoid the problem, the permanent magnet 436 is formed with magnetic material adapted to have such a magnetic force as to certainly attract the magnetic pin 446 or 448 if only the magnetic pin 446 is close to the permanent magnet 436. Accordingly, even though the rotation of the rotating disk 410 is stopped immediately before the magnetic pin 446 or 448 comes into contact with the permanent magnet 436, the magnetic pin 446 or 448 is attracted by and stuck to the permanent magnet 436. Therefore, the rotational position of the rotating disk 410 is surely held. It is noted that an appropriate material is selected for the permanent magnet 436 in view of Electro-Magnetic Interference (EMI).

Figure 7A:
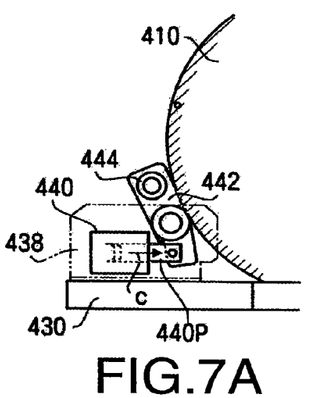
FIGS. 7A, 7B, and 7C are schematic diagrams showing a structure around a pinch roller in the embodiment according to one or more aspects of the present invention.
Figure 7B:
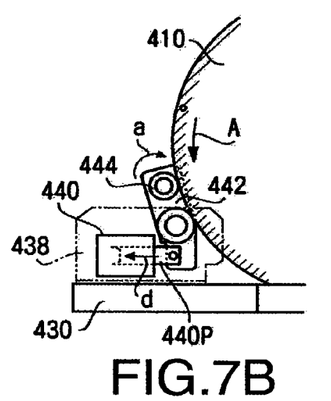
Figure 7C:
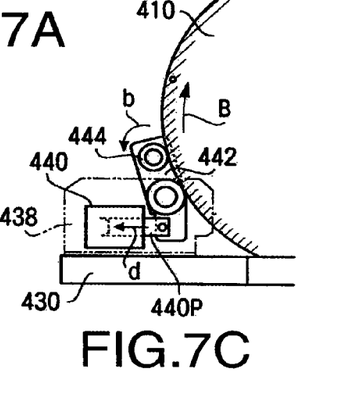

Furthermore, the structure around the rotating disk 410 is configured based on a fault tolerant design as mentioned below. Specifically, the structure around the rotating disk 410 is configured to be easily rotated by a manual operation in the case where the rotating disk 410 cannot be electrically driven to rotate, for example, due to malfunction of the DC motor 412. Such a configuration of the structure around the rotating disk 410 will be explained with reference to FIGS. 7A to 7C. FIGS. 7A to 7C schematically show the structure around the pinch roller 444 when viewed in an opposite direction to the viewing direction of FIG. 6 (namely, from a rear side of the processor 200). In FIGS. 7A to 7C, in the same way as FIG. 6, the structure around the pinch roller 444 is shown in a simplified manner for the sake of illustrative convenience.

The solenoid 440 is turned on through the control taken by the control circuit 240 when the switch 418 is switched. In addition, the solenoid 440 is turned off when one of the photo sensors 450 and 452 is detected to be in the transmitted state.

When the solenoid 440 is turned off, as illustrated in FIG. 7A, the solenoid 440 slides the plunger 440p in a direction indicated by an arrow "c" to move the distal end of the arm 442 in such a direction as to get the distal end away from the rotating disk 410. Thereby, the pinch roller 444 is rendered away from the rotating disk 410. At this time, there is no frictional force between the pinch roller 444 and the side circumferential surface of the rotating disk 410, the operator can easily rotate the rotating disk 410 by a manual operation.

In addition, when the solenoid 440 is turned on, as illustrated in FIGS. 7B and 7C, the solenoid 440 slides the plunger 440p in a direction indicated by an arrow "d" to move the distal end of the arm 442, namely, the pinch roller 444 toward the rotating disk 410. The solenoid 440 slides the plunger 440p so as to move the pinch roller 444 in a predetermined position, more specifically, in such a position as to be pressed against the side circumferential surface of the rotating disk 410 under a predetermined pressure. Thereby, a predetermined frictional force is generated between the pinch roller 444 and the side circumferential surface of the rotating disk 410. Thus, the pinch roller 444 can transmit the rotational driving force of the DC motor 412 to the rotating disk 410.

In other words, the pinch roller 444 is being pressed against the side circumferential surface of the rotating disk 410 only while the rotating disk 410 is electrically being driven to rotate (more specifically, during a period until one of the photo sensors 450 and 452 is detected to be in the transmitted state after the switch 418 is switched). The switch 418 is switched only when the light source that has been used is turned off, for instance, due to failure in the light source. Accordingly, the pinch roller 444 is regularly away from the side circumferential surface of the rotating disk 410. When the rotating disk 410 is not electrically driven, for example, due to failure in the DC motor 412, the operator can remove a part of the housing 202 to expose the structure around the rotating disk 410, and easily rotate the rotating disk 410 through a manual operation.

Thus, by employing the DC motor 412 as an actuator for rotating the rotating disk 410, it is possible to reduce a cost for manufacturing the light source apparatus (the structure around the rotating disk 410) and to simplify the configuration thereof. Additionally, any complicated pulse control for a stepping motor is not required, and thus it results in a simpler design. Moreover, the pinch roller 444 is employed as a transmission mechanism for transmitting the rotational driving force of the DC motor 412, instead of a gear as disclosed in the aforementioned '174 Publication. Therefore, the light source apparatus can be configured in a further simplified manner.

Hereinabove, the embodiment according to aspects of the present invention has been described. The present invention can be practiced by employing conventional materials, methodology and equipment. Accordingly, the details of such materials, equipment and methodology are not set forth herein in detail. In the previous descriptions, numerous specific details are set forth, such as specific materials, structures, processes, etc., in order to provide a thorough understanding of the present invention. However, it should be recognized that the present invention can be practiced without reapportioning to the details specifically set forth. In other instances, well known processing structures have not been described in detail, in order not to unnecessarily obscure the present invention.

Only an exemplary embodiment of the present invention and but a few examples of its versatility are shown and described in the present disclosure. It is to be understood that the present invention is capable of use in various other combinations and environments and is capable of changes or modifications within the scope of the inventive concept as expressed herein. For example, the present invention is capable of the following modifications.

For example, the light sources loaded in the light source apparatus are not limited to being two. More than three light sources may be provided in the light source apparatus.

In addition, the magnetic pins 446 and 448 may be configured with hard magnetic material (i.e., permanent magnetic material) while the permanent magnet 436 may be configured with soft magnetic material.

Further, the electronic endoscope system 10 is configured to conform to a frame sequential method. In this case, a rotating color filter may be disposed between the supporting plate 432 and the converging lens 420.

Furthermore, the sensor detection holes 456 and 458 may be formed with respective different shapes and respective different sizes so as to achieve respective different intensities of light beams passing therethrough. In this case, the control circuit 240 can detect a rotational angle of the rotating disk 410 based on output levels of the photo sensors 450 and 452.

Moreover, the control circuit 240 may be configured to control the solenoid 440 or the DC motor 412 to perform either a first operation of getting the pinch roller 444 away from the side circumferential surface of the rotating disk 410 or a second operation of driving the DC motor 412 to be stopped, when the magnetic pin 446 or 448 gets close to the permanent magnet 436 through the rotation of the rotating disk 410.

The present disclosure relates to the subject matter contained in Japanese Patent Application No. P2008-100241, filed on Apr. 8, 2008, which is expressly incorporated herein by reference in its entirety.

What is claimed is:

1. A light source apparatus configured to introduce light into an endoscope connected thereto, comprising:
   a housing;
   a plurality of light sources supported movably relative to the housing, the light sources being configured to emit light;
   a light introducing unit configured to introduce, into the endoscope, the light emitted by an intended one of the light sources which is located in such a position that an optical axis thereof corresponds to an optical axis of the light introducing unit;
   a detector configured to detect a misalignment between the optical axis of the light introducing unit and the optical axis of the intended light source; and
   a light source moving unit configured to move the intended light source to such a position that the optical axis of the intended light source corresponds to the optical axis of the light introducing unit when the misalignment is detected by the detector.

2. The light source apparatus according to claim 1, further comprising a light source holder configured to hold the light sources, the light source holder being supported movably relative to the housing,
   wherein the light source moving unit is configured to move the light source holder to change positions of the light sources relative to the light introducing unit.

3. The light source apparatus according to claim 2,
   wherein the light source holder includes a rotating disk supported rotatably relative to the housing, the light sources being attached to the rotating disk,
   wherein the light source moving unit is configured to rotate the rotating disk to change the positions of the light sources relative to the light introducing unit, and
   wherein the detector comprises:
      a hole formed in such a position on the rotating disk as to correspond to a position of each of the light sources in a radial direction of the rotating disk;
      a photo sensor configured to detect the hole; and
      a sensor output detector configured to detect the misalignment based on a detection result of the photo sensor.

4. The light source apparatus according to claim 1, further comprising a switch configured to select therethrough one of the light sources as the intended light source,
   wherein the detector is configured to detect the misalignment between the optical axis of the light introducing unit and the optical axis of the intended light source selected through the switch.

5. The light source apparatus according to claim 4, further comprising an electrical power supply configured to supply an electrical power required for emitting light, selectively to the intended light source selected through the switch.

6. The light source apparatus according to claim 1,
   wherein the light introducing unit includes a converging optical system configured to converge the light emitted by the intended light source and to introduce the converged light into a Light Carrying Bundle (LCB) of the endoscope.

7. The light source apparatus according to claim 3,
   wherein the light source moving unit comprises:
      a motor configured to generate a rotational driving force for rotating the rotating disk; and
      a roller configured to transmit the rotational driving force from the motor to the rotating disk such that the rotating disk is rotated.

8. The light source apparatus according to claim 7, wherein the motor is a DC motor.

9. The light source apparatus according to claim 2, further comprising a locking mechanism configured to lock the light source holder in such a position that the optical axis of the intended light source held by the light source holder corresponds to the optical axis of the light introducing unit when the light source moving unit does not move the light source holder.

10. The light source apparatus according to claim 3, further comprising a locking mechanism configured to lock the rotating disk in such a position that the optical axis of the intended light source attached to the rotating disk corresponds to the optical axis of the light introducing unit when the light source moving unit does not rotate the rotating disk.

11. The light source apparatus according to claim 10, wherein the locking mechanism comprises:
a first magnetic member fixed relative to the housing; and
a second magnetic member provided to the rotating disk, the second magnetic member being configured to establish contact with the first magnetic member through rotation of the rotating member, and
wherein the intended light source is firmly positioned relative to the light introducing unit by the second magnetic member stuck to the first magnetic member due to a magnetic attractive force generated therebetween when the light source moving unit does not rotate the rotating disk.

* * * * *